United States Patent
Viljoen et al.

(10) Patent No.: US 12,373,895 B2
(45) Date of Patent: Jul. 29, 2025

(54) METHODS, SYSTEMS, AND COMPUTER PROGRAM PRODUCTS FOR EVENT CORRELATION AND TRACKING IN A MULTI-STAKEHOLDER ENVIRONMENT

(71) Applicant: Change Healthcare Holdings, LLC, Nashville, TN (US)

(72) Inventors: Andre Viljoen, North Vancouver (CA); Arien Malec, Oakland, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 90 days.

(21) Appl. No.: 18/051,630

(22) Filed: Nov. 1, 2022

(65) Prior Publication Data

US 2024/0144380 A1    May 2, 2024

(51) Int. Cl.
*G06Q 40/08* (2012.01)
*G16H 10/60* (2018.01)

(52) U.S. Cl.
CPC ............. *G06Q 40/08* (2013.01); *G16H 10/60* (2018.01)

(58) Field of Classification Search
CPC ......... G06Q 40/08; G16H 10/60; G16H 40/20
See application file for complete search history.

(56) References Cited

U.S. PATENT DOCUMENTS

| | | | | |
|---|---|---|---|---|
| 2014/0249836 A1* | 9/2014 | Moran | ................ | G06Q 40/08 705/2 |
| 2015/0036138 A1* | 2/2015 | Watson | ................ | G01N 21/65 356/402 |
| 2017/0078094 A1* | 3/2017 | Olson | ................ | H04L 63/08 |
| 2017/0333124 A1* | 11/2017 | Gelbart | ................ | A61B 5/065 |
| 2018/0113987 A1* | 4/2018 | Zhu | ................ | G16H 40/63 |
| 2022/0037003 A1* | 2/2022 | Oliveira | ................ | G06F 8/38 |
| 2023/0123979 A1* | 4/2023 | Ulam | ................ | G06Q 40/08 705/2 |
| 2023/0342725 A1* | 10/2023 | Lindsay | ................ | G06Q 10/06316 |
| 2024/0111799 A1* | 4/2024 | Sabapathy | ................ | G06N 20/00 |

FOREIGN PATENT DOCUMENTS

CA    3141299 A1 * 12/2020 ........... B64C 39/024

OTHER PUBLICATIONS

Gowanit, Mobile claim management adoption in emerging insurance markets An exploratory study in Thailand, 2016, International Journal of Bank Marketing, vol. 34, No. 1, pp. 110-130. (Year: 2016).*

* cited by examiner

*Primary Examiner* — Christopher L Gilligan
(74) *Attorney, Agent, or Firm* — MARSHALL, GERSTEIN & BORUN LLP (57) ABSTRACT

A method includes receiving an event tracking query for a patient health care transaction from a requestor; receiving state transition updates for the event from ones of a plurality of different transaction processing entities that are independently controlled with respect to each other; mapping the state transition updates to a representational workflow model, which defines a plurality of tracking states; generating an event tracking result based on the mapping of the state transition updates to the representational workflow model and the plurality of different transaction processing entities; and communicating the event tracking result to the requestor.

16 Claims, 6 Drawing Sheets

METHODS, SYSTEMS, AND COMPUTER PROGRAM PRODUCTS FOR EVENT CORRELATION AND TRACKING IN A MULTI-STAKEHOLDER ENVIRONMENT

FIELD

The present inventive concepts relate generally to health care systems and services and, more particularly, to processing of transactions between health care providers, payors, and intermediaries.

BACKGROUND

Health care service providers have patients that pay for their care using a variety of different payors. For example, a medical facility or practice may serve patients that pay by way of different insurance companies including, but not limited to, private insurance plans, government insurance plans, such as Medicare, Medicaid, and state or federal public employee insurance plans, and/or hybrid insurance plans, such as those that are sold through the Affordable Care Act. When providers submit claims to the payors for payment, the claims may be processed by a variety of different intermediator entities, such as clearinghouses and the like, before reaching the payors. Similarly, when payors remit payment for claims or deny claims in whole or in part, the notifications may traverse a similar path through various intermediator entities before reaching the providers. Because claim submission and remittance may be a multi-step process that is split across multiple intermediaries, with many intermediaries being independently controlled with respect to each other, the particular sub-steps, nomenclature, identifiers, etc. used at the various intermediaries may share little in common. The inconsistent terminology and identifiers may make it difficult to track the state of a particular transaction, such as a claim or remittance, in the overall process.

SUMMARY

According to some embodiments of the inventive concept, a method comprises: receiving an event tracking query for a patient health care transaction from a requestor; receiving state transition updates for the event from ones of a plurality of different transaction processing entities that are independently controlled with respect to each other; mapping the state transition updates to a representational workflow model, which defines a plurality of tracking states; generating an event tracking result based on the mapping of the state transition updates to the representational workflow model and the plurality of different transaction processing entities; and communicating the event tracking result to the requestor.

In other embodiments, the plurality of different transaction processing entities comprises an originator, one or more intermediator entities, and one or more payors.

In still other embodiments, the event is submission of a health care claim; and the plurality of tracking states comprises ready for pickup by intermediator entity, picked up by intermediator entity, processed by intermediator entity, ready for pickup by payor, picked up by payor, processed by payor.

In still other embodiments, the event is a remittance for a health care claim; and the plurality of tracking states comprises ready for pickup by intermediator entity, picked up by intermediator entity, processed by intermediator entity, ready for pickup by originator, picked up by originator, processed by originator.

In still other embodiments, the event is submission of a first batch of health care claims; and the plurality of tracking states comprises ready for pickup by intermediator entity, picked up by intermediator entity, processed by intermediator entity, ready for pickup by payor, picked up by payor, processed by payor.

In still other embodiments, the event tracking result corresponds to the first batch of health care claims as a unit. The plurality of tracking states further comprises indicia associated with ones of the first batch of health care claims representing a demultiplexing of the ones of the first batch of health care claims from the batch and a multiplexing of the ones of the batch of health care claims back into a second batch between one or more providers and one or more payors.

In still other embodiments, the event tracking result corresponds to a respective one of the health care claims that is part of the first batch. The plurality of tracking states further comprises indicia associated with ones of the first batch of health care claims representing a demultiplexing of the ones of the first batch of health care claims from the batch and a multiplexing of the ones of the first batch of health care claims back into a second batch between one or more providers and one or more payors.

In still other embodiments, the state transition updates comprise mappings of identifiers between ones of the plurality of different transaction processing entities for items associated with the event and the items associated with the event comprise a filename, a claim identification, a payor identification, or a provider identification.

In still other embodiments, the plurality of tracking states comprises a plurality of high-level tracking states and a plurality of low-level tracking states; the plurality of high-level tracking states comprises ready for pickup by intermediator entity, picked up by intermediator entity, processed by intermediator entity, ready for pickup by payor, picked up by payor, processed by payor, ready for pickup by originator, picked up by originator, or processed by originator; and the plurality of low-level tracking states comprises an identity of one of the plurality of different transaction processing entities currently processing the event, or a custom defined state associated with one or more of the plurality of different transaction processing entities.

In still other embodiments, the event tracking result indicates a percentage of states complete in a life-cycle of the plurality of tracking states for the event; or the event tracking result indicates a current one of the plurality of tracking states for the event.

In still other embodiments, the event is submission of a request for prior authorization for a health care transaction, is submission of an insurance coverage eligibility request for a health care procedure, is submission of a health care claim, or is submission of a health care claim remittance.

In some embodiments of the inventive concept, a system comprises: a processor; and a memory coupled to the processor and comprising computer readable program code embodied in the memory that is executable by the processor to perform operations comprising: receiving an event tracking query for a patient health care transaction from a requestor; receiving state transition updates for the event from ones of a plurality of different transaction processing entities that are independently controlled with respect to each other; mapping the state transition updates to a representational workflow model, which defines a plurality of tracking states; generating an event tracking result based on the mapping of the state transition updates to the representational workflow model and the plurality of different transaction processing entities; and communicating the event tracking result to the requestor.

In further embodiments, the plurality of different transaction processing entities comprises an originator, one or more intermediator entities, and one or more payors.

In still further embodiments, the event is submission of a first batch of health care claims; the event tracking result corresponds to the first batch of health care claims as a unit; and the plurality of tracking states further comprises indicia associated with ones of the first batch of health care claims representing a demultiplexing of the ones of the first batch of health care claims from the first batch and a multiplexing of the ones of the first batch of health care claims back into a second batch between one or more providers and one or more payors.

In still further embodiments, the event tracking result corresponds to a respective one of the health care claims that is part of the first batch.

In still further embodiments, the state transition updates comprise mappings of identifiers between ones of the plurality of different transaction processing entities for items associated with the event; and the items associated with the event comprise a filename, a claim identification, a payor identification, or a provider identification.

In still further embodiments, the plurality of tracking states comprises a plurality of high-level tracking states and a plurality of low-level tracking states; the plurality of high-level tracking states comprises ready for pickup by intermediator entity, picked up by intermediator entity, processed by intermediator entity, ready for pickup by payor, picked up by payor, processed by payor, ready for pickup by originator, picked up by originator, or processed by originator; and the plurality of low-level tracking states comprises an identity of one of the plurality of different transaction processing entities currently processing the event, or a custom defined state associated with one or more of the plurality of different transaction processing entities.

In still further embodiments, the event tracking result indicates a percentage of states complete in a life-cycle of the plurality of tracking states for the event; or the event tracking result indicates a current one of the plurality of tracking states for the event.

In still further embodiments, the event is submission of a request for prior authorization for a health care transaction, is submission of an insurance coverage eligibility request for a health care procedure, is submission of a health care claim, or is submission of a health care claim remittance.

In some embodiments of the inventive concept, a computer program product comprises: a non-transitory computer readable storage medium comprising computer readable program code embodied in the medium that is executable by a processor to perform operations comprising: receiving an event tracking query for a patient health care transaction from a requestor; receiving state transition updates for the event from ones of a plurality of different transaction processing entities that are independently controlled with respect to each other; mapping the state transition updates to a representational workflow model, which defines a plurality of tracking states; generating an event tracking result based on the mapping of the state transition updates to the representational workflow model and the plurality of different transaction processing entities; and communicating the event tracking result to the requestor.

It is noted that aspects described with respect to one embodiment may be incorporated in different embodiments although not specifically described relative thereto. That is, all embodiments and/or features of any embodiments can be combined in any way and/or combination. Moreover, other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

In the following detailed description, numerous specific details are set forth to provide a thorough understanding of embodiments of the inventive concept. However, it will be understood by those skilled in the art that embodiments of the inventive concept may be practiced without these specific details. In some instances, well-known methods, procedures, components, and circuits have not been described in detail so as not to obscure the inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "provider" may mean any person or entity involved in providing health care products and/or services to a patient.

Embodiments of the inventive concept are described herein in the context of providing a tracking system for a multi-stakeholder environment. The tracking system for a multi-stakeholder environment described herein may be configured to transform a memory of a computer system to include one or more data structures, such as, but not limited to, arrays, extensible arrays, linked lists, binary trees, balanced trees, heaps, stacks, and/or queues. These data structures can be configured or modified through the mapping of states associated with a system independent model component of the tracking system with dependent components of the tracking system, which are associated with states, including terminologies, identifiers, and the like, of different intermediaries used to process health care transactions, such as claims and remittances. These intermediaries may be independently controlled with respect to each other and, therefore, may have their own universe of conventions with respect to state identifiers, terminologies, and the like. By separating the tracking into system independent and dependent parts, the tracking system may allow for consolidated tracking of events among disparate and disconnected systems.

Some embodiments of the inventive concept stem from a realization that transactions between providers and payors in the health care field, such as claim submission, payment remittance, and/or claim denial, may use multiple intermediator entities to process these transactions. As these intermediaries may be independently controlled with respect to each other and may not share a common convention with respect to the language or terminology used in identifying states and/or processing the transaction, it may be difficult to track the state of a particular transaction, such as a claim or remittance.

Some embodiments of the inventive concept may provide a tracking system for a multi-stakeholder environment in which tracking is separated into system dependent and independent parts. The states in the independent part of the tracking system and the states in the dependent of the tracking system may be mapped to one another, which may allow the tracking of transactions across multiple different intermediator entities without knowing the specific terminologies, identifiers, and the like for processing states in those systems.

It will be understood that embodiments of the inventive concept are described herein with respect to event tracking in a health care environment in which the event may be a transaction, such as a claim submission by a provider or remittance by a payor, for example. It will be understood, however, that embodiments of the inventive concept are applicable generally to tracking events across multiple actors that are independently controlled with respect to each other and may use different terminologies, identifiers, and the like for processing the events.

Figure 1:
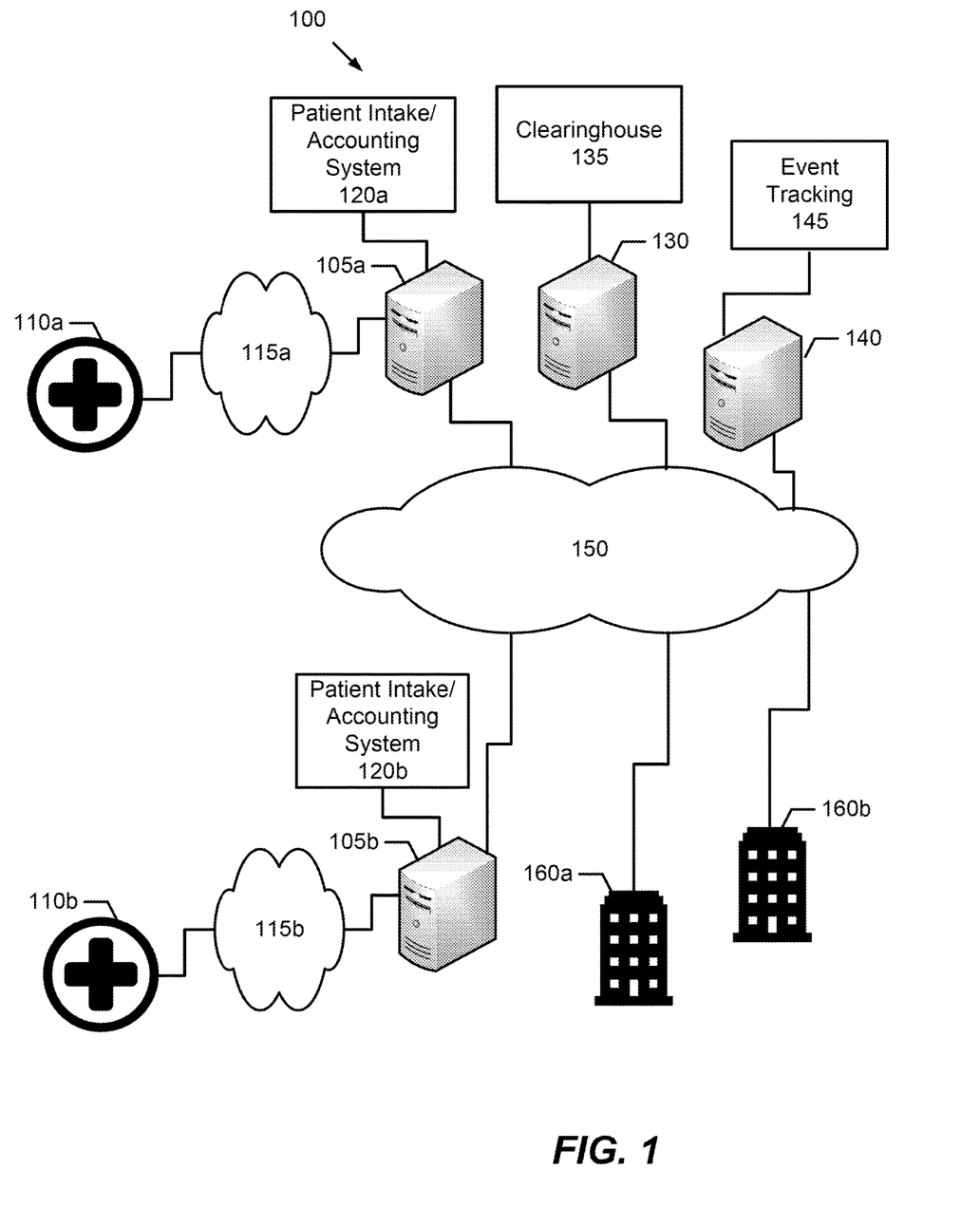
FIG. 1 is a block diagram that illustrates a communication network including an event tracking system for a multi-stakeholder environment in accordance with some embodiments of the inventive concept.

Referring to FIG. 1, a communication network 100 including an event tracking system in a multi-stakeholder environment, in accordance with some embodiments of the inventive concept, may comprise multiple health care provider facilities or practices 110a, 110b. Each health care provider facility or practice may represent various types of organizations that are used to deliver health care services to patients via health care professionals, which are referred to generally herein as "providers." The providers may include, but are not limited to, hospitals, medical practices, mobile patient care facilities, diagnostic centers, lab centers, pharmacies, and the like. The providers may operate by providing health care services for patients and then invoicing one or more payors 160a and 160b for the services rendered. The payors 160a and 160b may include, but are not limited to, providers of private insurance plans, providers of government insurance plans (e.g., Medicare, Medicaid, state, or federal public employee insurance plans), providers of hybrid insurance plans (e.g., Affordable Care Act plans), private of private medical cost sharing plans, and the patients themselves. Two provider facilities 110a, 110b are illustrated in FIG. 1 with the first provider including a first patient intake/accounting system server 105a accessible via a network 115a. The first patient intake/accounting system server 105a may be configured with a patient intake/accounting system module 120a to manage the intake of patients for appointments and to generate invoices for payors for services and products rendered through the provider 110a. The network 115a communicatively couples the first patient intake/accounting system server 105a to other devices, terminals, and systems in the provider's facility 110a. The network 115a may comprise one or more local or wireless networks to communicate with first patient intake/accounting system server 105a when the first patient intake/accounting system server 105a is located in or proximate to the health care service provider facility 110a. When the first patient intake/accounting system server 105a is in a remote location from the health care facility, such as part of a cloud computing system or at a central computing center, then the network 115a may include one or more wide area or global networks, such as the Internet. The second provider facility 110b is similar to the first provider facility 110a and includes a second patient intake/accounting system server 105b, which is configured with a patient intake/accounting system server 120b. The second patient intake/accounting system server 105b is coupled to other devices, terminals, and systems in the provider's facility 110b via a network 115b.

According to embodiments of the inventive concept, one or more intermediators may be used between a health care service provider and a payor for processing claims submitted by providers to payors and for processing remittances or claim denials submitted by payors to providers. An intermediary server 130 may include a clearinghouse system module 135 that may be configured to receive incoming claims from one or more providers 110a, 110b, communicate the claims to the appropriate payor 160a, 160b or to another intermediator entity, and route the payor responses back to another intermediator entity or to the appropriate provider 110a, 110b by way of the patient intake/accounting systems 120a, 120b. Although only one intermediary server 130 is shown, there may be multiple intermediator entities between providers and payors that are configured to process claims and responses thereto. These intermediator entities may be independently controlled with respect to each other and may not share a common convention with respect to the language or terminology used in identifying states and/or processing the claims, remittance, or other transaction.

The communication network 100 further includes an event tracking server 140 that includes an event tracking module 145. The event tracking module 145 may be configured to a multi-stakeholder tracking function in which tracking is separated into system dependent and independent parts. A mapping functionality may be provided in which the states in the independent part of the tracking system and the states in the dependent part of the tracking system are mapped to one another. This may allow tracking of transactions, such as claims processing, remittance processing, and the like across multiple intermediator entities without knowing the particular conventions, identifiers, terminologies, vocabularies, and the like for processing events or transactions in those systems.

A network 150 couples the event tracking server 140 to the patient intake/accounting system servers 105a, 105b, the one or more intermediary servers 130, and the payors 160*a* and 160*b*. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The event correlation and tracking service provided through the event tracking server 140 and the event tracking module 145 for tracking events in a multi-stakeholder environment may, in some embodiments, be embodied as a cloud service. For example, health care service providers and/or payors may access the event tracking system as a Web service. In some embodiments, the event tracking system service may be implemented as a Representational State Transfer Web Service (RESTful Web service).

Although FIG. 1 illustrates an example communication network including an event tracking service for tracking events in a multi-stakeholder environment, it will be understood that embodiments of the inventive subject matter are not limited to such configurations, but are intended to encompass any configuration capable of carrying out the operations described herein.

Figure 2:
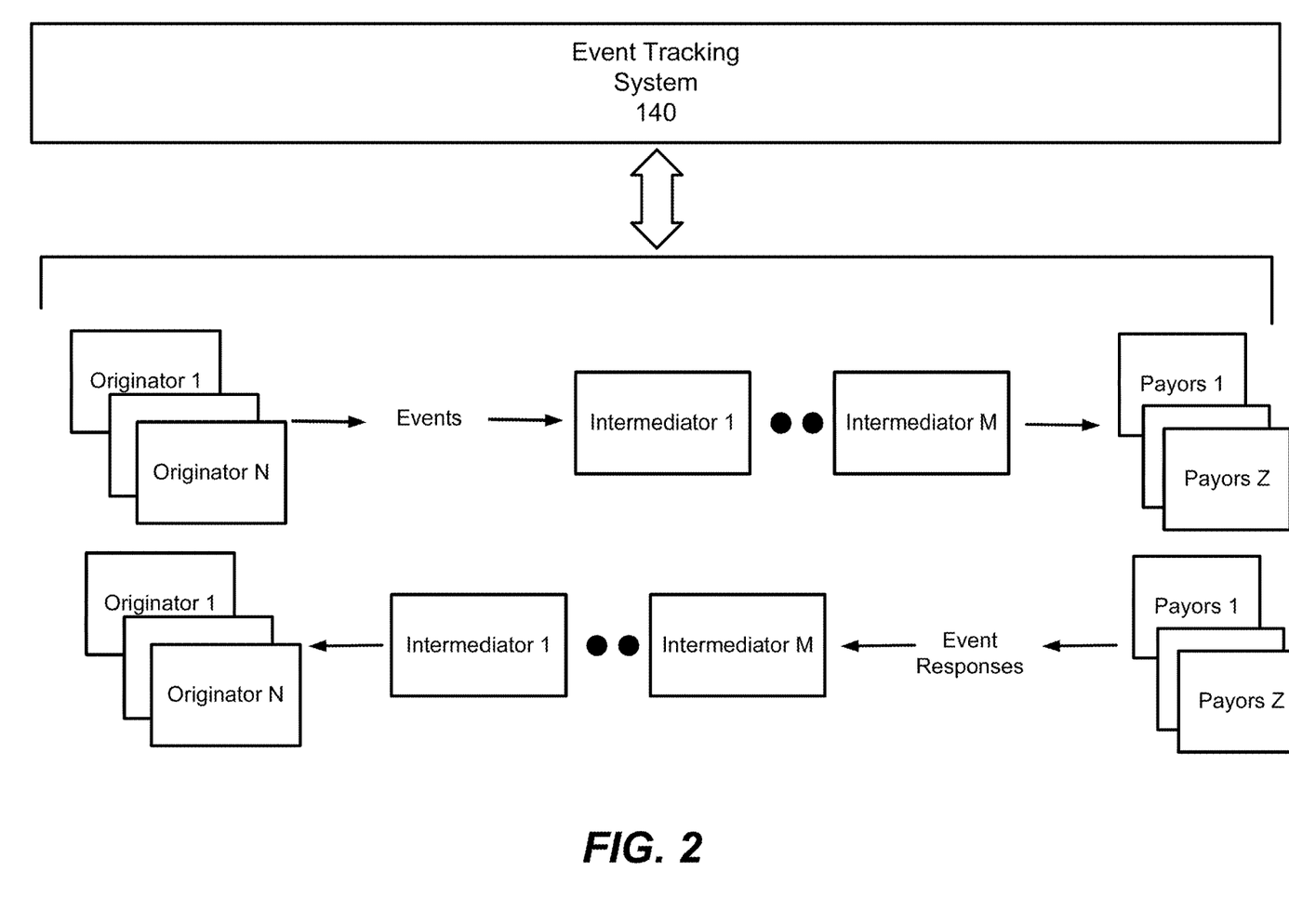
FIG. 2 is a block diagram that illustrates the event flow between originators, intermediaries, and payors that is tracked using an event tracking system for a multi-stakeholder environment in accordance with to some embodiments of the inventive concept.

FIG. 2 is a block diagram that illustrates the event tracking system 140 for tracking events in a multi-stakeholder environment according to some embodiments of the inventive concept. According to some embodiments, the event tracking system 140 may communicate with one or more originators 1-N, such as health care providers, and one or more payors 1-Z. The originators 1-N may submit health care claims to the payors 1-Z for payment and the payors may submit responses in reply thereto in the form of remittances and/or as claim denials in whole or in part. These claim submissions and responses thereto may be events or transactions the status of which may be tracked through the event tracking system 140. The events and event responses may be processed by one or more intermediator entities 1-M, which operate between the originators 1-N and the payors 1-Z. At least some of these intermediators may be independently controlled with respect to each other and may not share a common convention with respect to the vocabulary, terminology, identifiers, and the like for naming states, identifying processing operations, etc. As a result, it may be difficult to track the state of a particular event due to the varied ways in which events are described in the originators 1-N, the intermediator entities 1-M, and the payors 1-Z. This problem may be further complicated by the way in which originators submit claims for payment. Rather than submit claims individually, providers may group claims into a batch and submit an entire batch together periodically, which may be destined for one payor or, more typically, many different payors. The intermediator entities may, therefore, unpack or de-multiplex the batch of claims for processing and ultimately communicate the claims individual or in groups or batches to the appropriate payors 1-Z. As payors return remittances or claim denials, the intermediators may process these responses and multiplex the responses back together as batch for returning to the originator. The claim responses may be further de-multiplexed from the batch in the originator, as an originator may include multiple sub-entities, e.g., a medical group that includes a coalition of multiple smaller practices. Intermediator entities may also switch between batch mode and serial mode transmission for items communicated between endpoints. Although described above with respect to the event being submission of a health care claim and the tracking being related to determining the status of the claim, it will be understood that embodiments of the inventive concept are applicable to other types of events including, but not limited to, submission of a request for prior authorization for a health care transaction, submission of an insurance coverage eligibility request for a health care procedure, and/or submission of a health care claim remittance The event tracking system 140 may be configured to divide the tracking into independent and dependent parts as described above. The dependent parts are associated with the various entities in the event chain, i.e., originators 1-N, intermediator entities 1-M, and payors 1-Z, at least some of which may be independently controlled with respect to one another and, therefore, do not share a common nomenclature with respect to states, processes, etc. that may be used to track events through the chain. The independent part of the event tracking system 140 may provide a system independent representation of the various states that an event or transaction may traverse. This may allow a user to track events or transactions across different systems, which are independently controlled and may not share a common nomenclature for event states, processes, and the like, without knowing the specific terminologies or identifiers of each of the intermediator or end-point systems. As an example, a submitter may communicate a file under a file name to a batch file system, which might rename it (e.g., to a name that identifies the submitter and date/time the file was received), and a third system may pick the file up and rename it again and split the file into sub-transactions. By keeping track of each system's identifiers and terminology and mapping these identifiers to a system independent representation or nomenclature, the event tracking system 140 may be configured to decouple the processing operations of logically independent systems, e.g., the end point entities and intermediator entities, while providing comprehensive tracking information.

Figure 3:
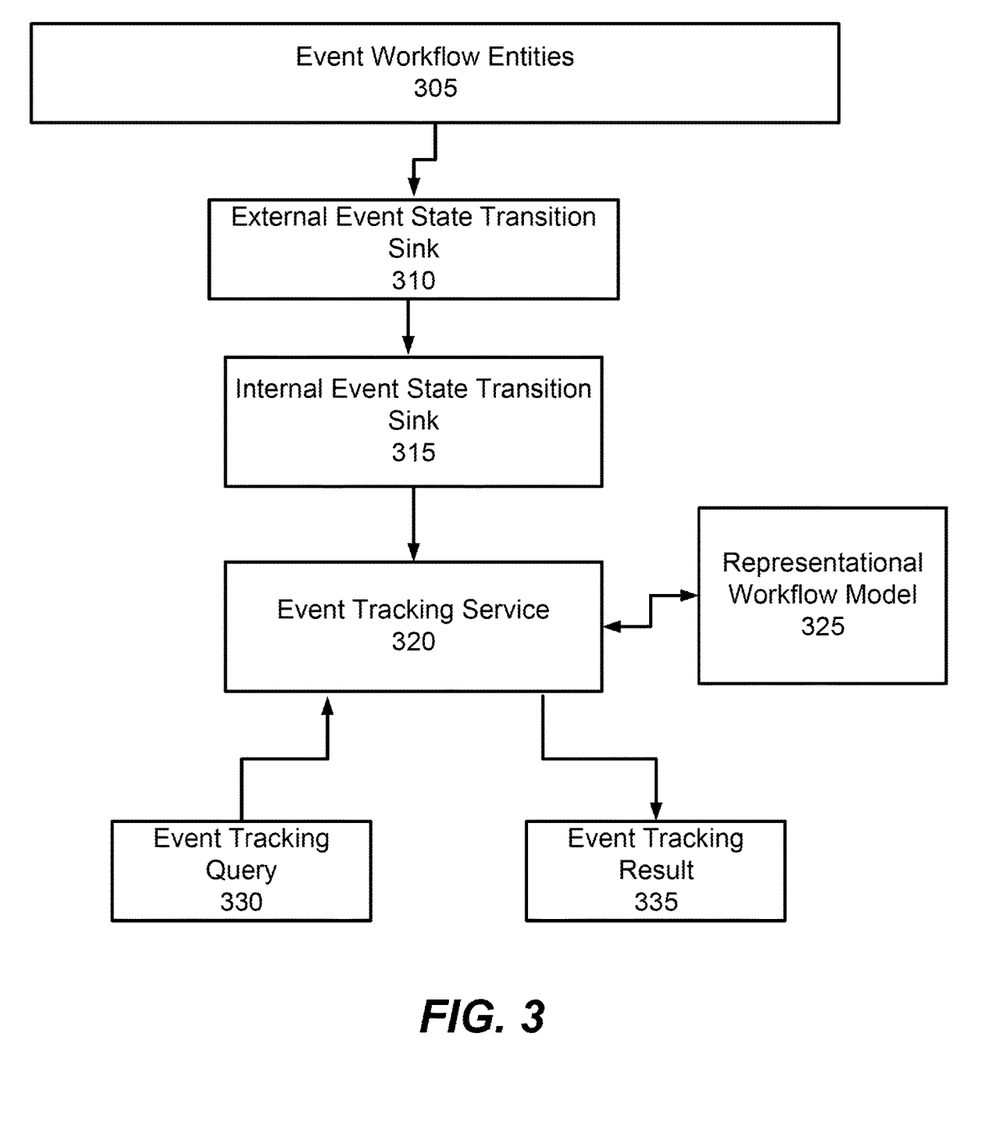
FIG. 3 is a block diagram that illustrates an event tracking system for a multi-stakeholder environment in accordance with to some embodiments of the inventive concept.

FIG. 3 is a block diagram that illustrates an event tracking system for a multi-stakeholder environment in accordance with some embodiments of the inventive concept. Referring to FIG. 3, the event tracking system may receive events or transactions from event workflow entities 305, which may be end point entities, such as the originators 1-N and payors 1-Z of FIG. 2 and/or the intermediator entities 1-M of FIG. 2. An external event state transition sink 310 may receive information from the event workflow entities 305 identifying the particular operations taking place in these independent systems using their vocabulary, identifiers, etc. Examples of these events may be receiving a batch file with a file name, changing the name of the batch file, exploding the batch file into individual elements, and the like. The internal event state transition sink 315 may take the information from the external event state transition sink and normalize the names, identifiers and the like. Thus, the combination of the external event state transition sink 310 and the internal event state transition sink 315 may be configured to collect event, transaction, or state transition information from various entities in a processing chain, at least some of which are independently controlled with respect to each other and may use different nomenclature for identifying events, transactions, and state transitions, and may normalize this information to descriptors used by the event tracking system 140. The event tracking service 320 may be configured to map the event information collected from the various entities in the processing chain to a representational workflow model 325 that identifies system independent tracking states that are representative of the various events, transactions, state transitions and the like taking place in the various processing chain entities. For example, some system independent tracking states may include ready for pickup by intermediator entity, picked up by intermediator entity, processed by intermediator entity, ready for pickup by an endpoint entity, picked up by an endpoint entity, processed by an endpoint entity, etc. The event tracking service may map system specific state information, such as file name information, which may include name changes, the addition or subtraction of prefixes and extensions, the association of flags or other indicia with the names, and the like, which may be specific or unique to each intermediator entity and map this information to a system independent tracking state. As a specific example, when an intermediator entity receives a file and modifies the file name to append RCVD to the file name, the event tracking service 320 may map this to a system independent tracking state defined as picked up by the intermediator entity. When the intermediator entity associates a completed flag with the file name, then the event tracking service may map this to a system independent tracking state defined as processed by the intermediator entity. This may allow actors, such as submitters, e.g., health care providers or payors, to submit event tracking queries 330 for events, such as claims or remittances, and obtain event tracking results 335 without needing to know the particulars of how each system in the end-to-end processing chain identifies the various events, transactions, state transitions, and the like.

Figure 4:
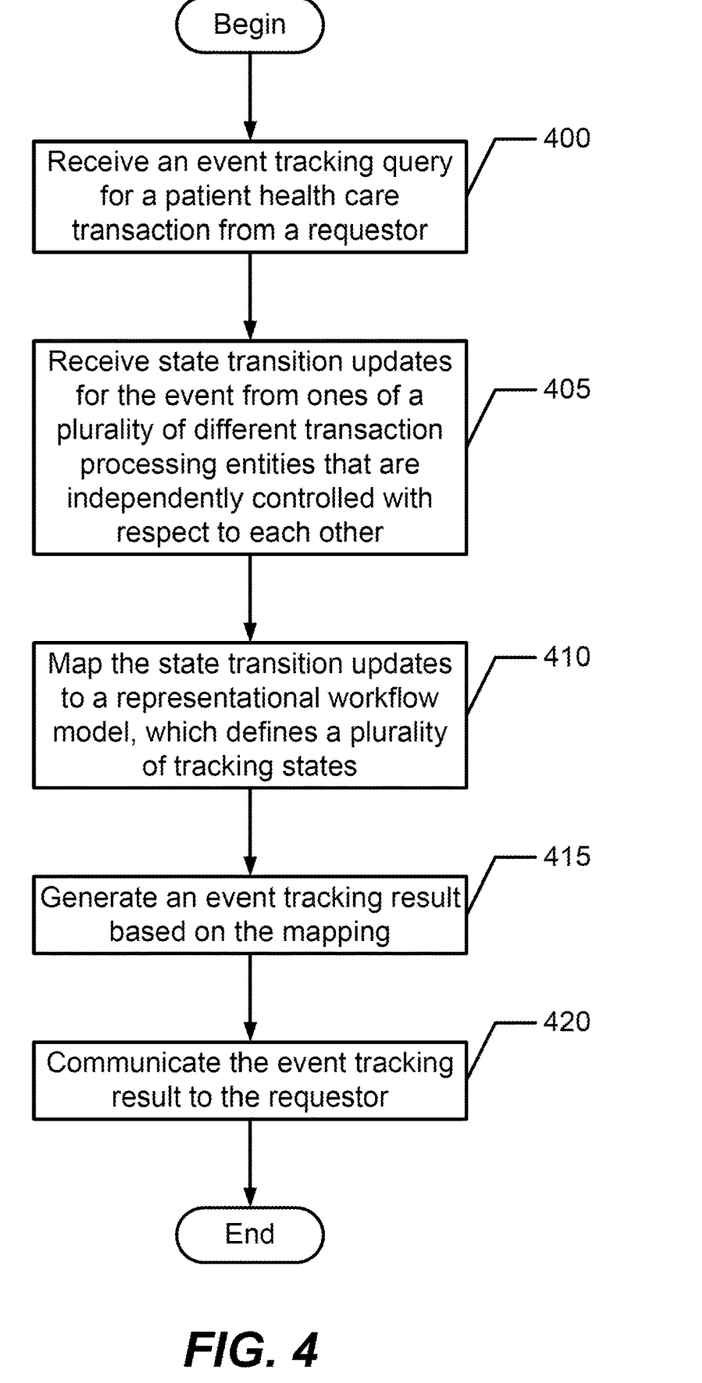
FIG. 4 is a flowchart that illustrates operations for tracking events in a multi-stakeholder environment in accordance with some embodiments of the inventive concept.

FIG. 4 is a flowchart that illustrates operations for tracking events in a multi-stakeholder environment in accordance with some embodiments of the inventive concept. Operations begin at block 400 where an event tracking query is received for a patient health care transaction from a requestor. State transition updates for the event are received at block 405 from respective ones of a plurality of different transaction processing entities, e.g., originators, intermediator entities, and payors, which are independently controlled with respect to each other. The state transition updates reflect the mappings of identifiers between the various transaction processing entities for items associated with the event. These items may include, but are not limited to, filenames, claim identifications, payor identifications, and/or provider identifications. That is, the transaction processing entities may have their own internal or system specific mappings of names, identifiers, and the like for processing an item. For example, a file may be received at an intermediator entity with the name of "myfile." The intermediator entity upon receipt may rename the file myfile_092326. Upon processing the file, the intermediator may rename the file myfile_092326exe. The state transition updates are mapped to a representational workflow model, which defines a plurality of higher level, system independent tracking states at block 410. Using the foregoing example, an update that the file has been renamed myfile_092326xe may be mapped to the system independent tracking state, such as processed by intermediator entity where the intermediator entity is identified by name. When the event is submission of a health care claim, the plurality of tracking states may comprise ready for pickup by intermediator entity, picked up by intermediator entity, processed by intermediator entity, ready for pickup by payor, picked up by payor, processed by payor. When the event is a remittance for a health care claim, the plurality of tracking states may comprise ready for pickup by intermediator entity, picked up by intermediator entity, processed by intermediator entity, ready for pickup by originator, picked up by originator, processed by originator. When the event is submission of a batch of health care claims, the plurality of tracking states may comprise ready for pickup by intermediator entity, picked up by intermediator entity, processed by intermediator entity, ready for pickup by payor, picked up by payor, processed by payor. For submission of a batch, which can be anything that can be grouped together, such as health care claims, health care claim remittances, insurance coverage eligibility requests, and the like, the tracking states may comprise indicia that are associated with ones of the batch that represent demultiplexing of the items in the batch and multiplexing the items in the batch between endpoints, such as between one or more providers and one or more payors. In accordance with some embodiments, the items in a first batch may be demultiplexed from the first batch and multiplexed back into a second batch between the endpoints and the first and second batches may correspond to the same batch or may be different batches. That is, a first batch of items may be demultiplexed and multiplexed back into one or more batches that are different from the first batch. This may facilitate tracking of events between one-to-one endpoints, one-to-many endpoints, and many-to-many endpoints. The tracking states may also comprise high-level tracking states, such as those listed above, e.g., ready for pickup by intermediator entity, picked up by intermediator entity, processed by intermediator entity, ready for pickup by payor, picked up by payor, processed by payor, ready for pickup by originator, picked up by originator, or processed by originator as well as low-level tracking states (tracking states with a finer granularity), such as the identity of one of the transaction processing entities current processing an event or a custom defined state associated with one or more of the transaction processing entities.

An event tracking result may be generated based on the mapping at block 415. In the case of processing a batch of health care claims, the event tracking result may correspond to the batch of health care claims as a unit or to one or more respective ones of the health care claims that are part of the batch in accordance with different embodiments of the inventive concept. In other embodiments, the event tracking result may indicate a percentage of states complete in a life-cycle of the plurality of tracking states for the event, or, in other embodiments, a current one of the plurality of tracking states for the event. The event tracking result may be communicated to the requestor at block 420.

While embodiments of the inventive concept have been described with respect to a health care environment in which the status of health care claims and remittances may be tracked, it will be understood that embodiments of the inventive concept are applicable generally to tracking of events across multiple processing systems that are independently controlled with respect to each other and may use different nomenclature with respect to processing states. Moreover, embodiments of the inventive concept may also be applicable to other health care environment events, such as requests for prior authorization for a health care transaction.

Figure 5:
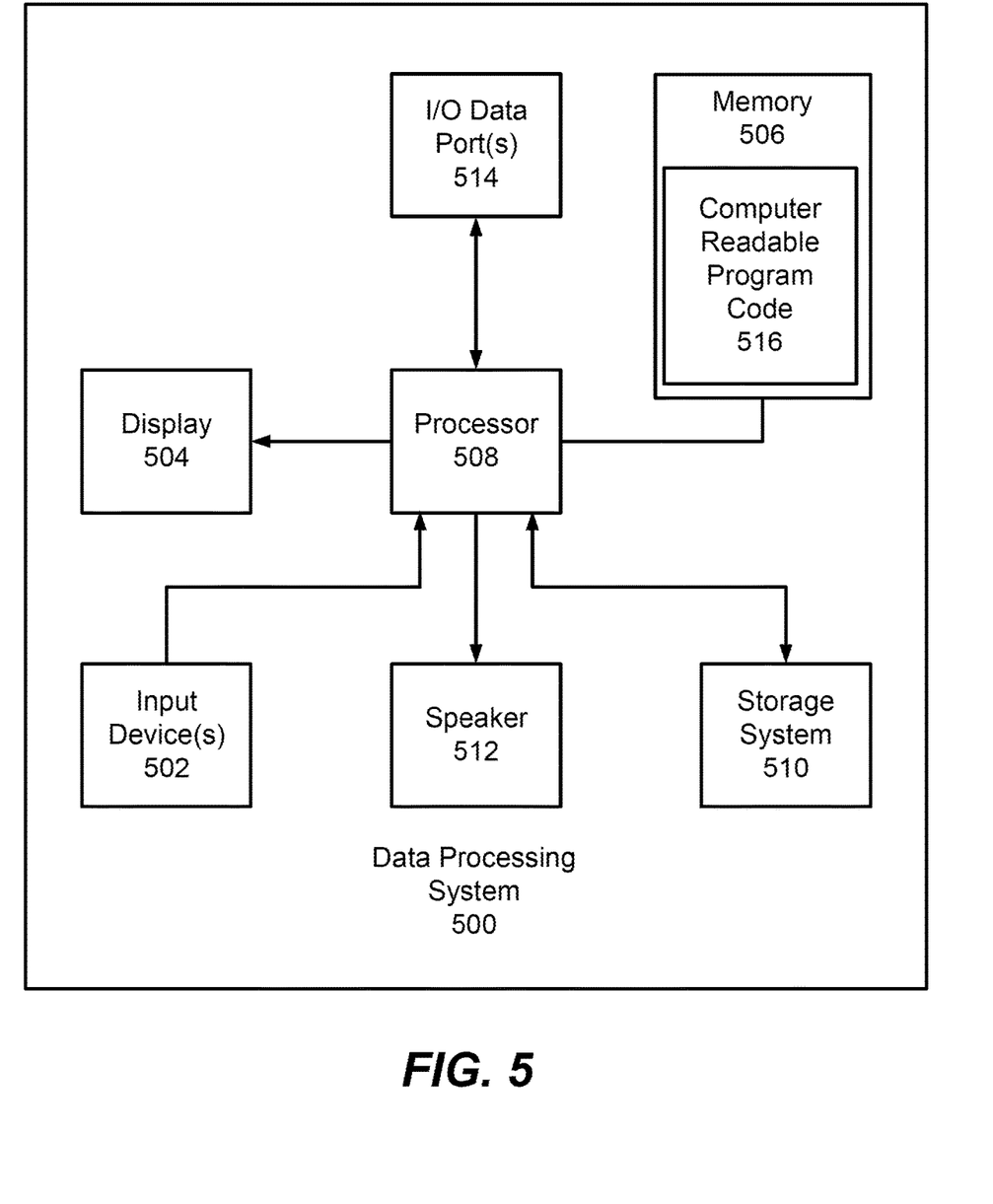
FIG. 5 is a data processing system that may be used to implement an event tracking system for a multi-stakeholder environment in accordance with some embodiments of the inventive concept.

Referring now to FIG. 5, a data processing system 500 that may be used to implement the event tracking server 145 of FIG. 1, in accordance with some embodiments of the inventive concept, comprises input device(s) 502, such as a keyboard or keypad, a display 504, and a memory 506 that communicate with a processor 508. The data processing system 500 may further include a storage system 510, a speaker 512, and an input/output (I/O) data port(s) 514 that also communicate with the processor 508. The processor 508 may be, for example, a commercially available or custom microprocessor. The storage system 510 may include removable and/or fixed media, such as floppy disks, ZIP drives, hard disks, or the like, as well as virtual storage, such as a RAMDISK. The I/O data port(s) 514 may be used to transfer information between the data processing system 500 and another computer system or a network (e.g., the Internet). These components may be conventional components, such as those used in many conventional computing devices, and their functionality, with respect to conventional operations, is generally known to those skilled in the art. The memory 506 may be configured with computer readable program code 516 to facilitate tracking of events in a multi-stakeholder environment according to some embodiments of the inventive concept.

Figure 6:
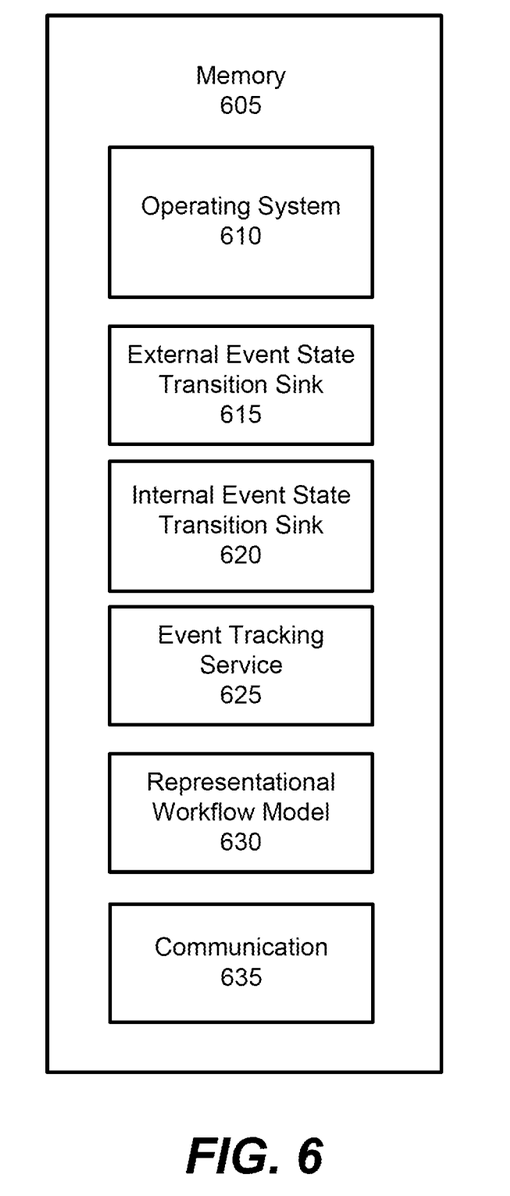
FIG. 6 is a block diagram that illustrates a software/hardware architecture for use in in an event tracking system for a multi-stakeholder environment in accordance with some embodiments of the inventive concept.

FIG. 6 illustrates a memory 605 that may be used in embodiments of data processing systems, such as the event tracking server 140 of FIG. 1 and the data processing system of FIG. 5, respectively, to facilitate event tracking in a multi-stakeholder environment. The memory 605 is representative of the one or more memory devices containing the software and data used for facilitating operations of the event tracking server 140 and the event tracking module 145 as described herein. The memory 605 may include, but is not limited to, the following types of devices: cache, ROM, PROM, EPROM, EEPROM, flash, SRAM, and DRAM. As shown in FIG. 6, the memory 605 may contain six or more categories of software and/or data: an operating system 610, an external event state transition sink 615, an internal event state transition sink 620, an event tracking service 625, a representational workflow model 630, and a communication module 635. In particular, the operating system 610 may manage the data processing system's software and/or hardware resources and may coordinate execution of programs by the processor. The external event state transition sink module 615 may be configured to perform one or more of the operations described above with respect to the event tracking server 140 and event tracking module 145, the external event state transition sink block 310, and FIG. 4. The internal event state transition sink module 620 may be configured to perform one or more of the operations described above with respect to the event tracking server 140 and event tracking module 145, the internal event state transition sink block 315, and FIG. 4. The event tracking service module 625 may be configured to perform one or more of the operations described above with respect to the event tracking server 140 and event tracking module 145, the event tracking service block 320, and FIG. 4. The representational workflow model module 630 may be configured to perform one or more of the operations described above with respect to the event tracking server 140 and event tracking module 145, the representational workflow model 325, and FIG. 4. The communication module 635 may be configured to facilitate communication between the event tracking server 140 and a service entity and the originators 1-N, intermediator entities 1-M, and/or the payors 1-Z of FIG. 2 along with any requesting entities that seek a tracking result of an event processed through the originators 1-N, intermediator entities 1-M, and/or the payors 1-Z of FIG. 2.

Although FIG. 6 illustrates hardware/software architectures that may be used in data processing systems, such as the event tracking server 140 of FIG. 1 and the data processing system of FIG. 5, respectively, in accordance with some embodiments of the inventive concept, it will be understood that embodiments of the present invention are not limited to such a configuration but is intended to encompass any configuration capable of carrying out operations described herein.

Computer program code for carrying out operations of data processing systems discussed above with respect to FIGS. 1-6 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the event tracking server 140 and the data processing system 500 of FIG. 5 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system." The functionality provided by the event processing server 140 may be embodied as a single server or embodied as separate servers in accordance with different embodiments of the inventive concept.

The data processing apparatus described herein with respect to FIGS. 1-6 may be used to facilitate tracking of events in a multi-stakeholder environment according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 605 when coupled to a processor includes computer readable program code that, when executed by the processor, causes the processor to perform operations including one or more of the operations described herein with respect to FIGS. 1-4

Some embodiments of the inventive concept may provide a tracking system for a multi-stakeholder environment in which tracking is separated into system dependent and independent parts. By separating the tracking into system independent and dependent parts, the tracking system may allow for consolidated tracking of events among disparate and disconnected systems, which may be independently controlled with respect to each other and may not share a common convention with respect to the language or terminology used in identifying states and/or processing events.

Further Definitions and Embodiments

In the above-description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A computer-implemented method, comprising:
    receiving, by one or more processors, an event tracking query for a patient healthcare transaction from a requestor;
    receiving, by the one or more processors, a set of state transition updates for an event associated with the event tracking query from a set of different transaction processing entities that are independently controlled with respect to each other, the set of state transition updates received from the set of different transaction processing entities including one or both of (i) a set of different state identifiers and (ii) a set of different terminologies, wherein the event comprises a batch of healthcare claims;
    demultiplexing, by the one or more processors, the batch of healthcare claims associated with the set of state transition updates;
    mapping, by the one or more processors, the set of state transition updates to a representational workflow model, which defines a set of tracking states;
    generating, by the one or more processors, an event tracking result based on the mapping of the set of state transition updates to the representational workflow model and the set of different transaction processing entities;
    multiplexing, by the one or more processors, the batch of healthcare claims associated with the mapped set of state transition updates; and
    transmitting, by the one or more processors, the event tracking result corresponding to the multiplexed batch of healthcare claims to the requestor.

2. The computer-implemented method of claim 1, wherein the set of different transaction processing entities comprises an originator, one or more intermediator entities, and one or more payors.

3. The computer-implemented method of claim 2, wherein the event comprises submission of a healthcare claim; and
    wherein the set of tracking states comprises one or more states indicating the submission being ready for pickup by a first intermediator entity of the one or more intermediator entities, picked up by the first intermediator entity, processed by the first intermediator entity, ready for pickup by a first payor of the one or more payors, picked up by the first payor, or processed by the first payor.

4. The computer-implemented method of claim 2, wherein the event comprises a remittance for a healthcare claim; and wherein the set of tracking states comprises one or more states indicating the remittance being ready for pickup by a first intermediator entity of the one or more intermediator entities, the remittance being picked up by the first intermediator entity, the remittance being processed by the first intermediator entity, the remittance being ready for pickup by the originator, the remittance being picked up by the originator, or the remittance being processed by the originator.

5. The computer-implemented method of claim 2, wherein the event comprises submission of a first batch of healthcare claims; and wherein the set of tracking states comprises one or more states indicating the submission being ready for pickup by a first intermediator entity of the one or more intermediator entities, picked up by the first intermediator entity, processed by the first intermediator entity, ready for pickup by a first payor of the one or more payors, picked up by the first payor, or processed by the first payor.

6. The computer-implemented method of claim 1, wherein the set of state transition updates comprises mappings of identifiers between ones of the set of different transaction processing entities for a set of items associated with the event; and wherein the set of items associated with the event comprise at least one of a filename, a claim identification, a payor identification, or a provider identification.

7. The computer-implemented method of claim 2, wherein the set of tracking states comprises a set of high-level tracking states and a set of low-level tracking states;

wherein the set of high-level tracking states comprises one or more states indicating that a submission or a remittance for a healthcare claim is at least one of the submission or the remittance being ready for pickup by a first intermediator entity of the one or more intermediator entities, picked up by the first intermediator entity, processed by the first intermediator entity, ready for pickup by a first payor of the one or more payors, picked up by the first payor, processed by the first payor, ready for pickup by the originator, picked up by the originator, or processed by the originator; and wherein the set of low-level tracking states comprises at least one of an identity of one of the set of different transaction processing entities currently processing the event or a custom defined state associated with one or more of the set of different transaction processing entities.

8. The computer-implemented method of claim 1, wherein the event tracking result indicates at least one of:
a percentage of states complete in a life-cycle of the set of tracking states for the event; or
a current one of the set of tracking states for the event.

9. The computer-implemented method of claim 1, wherein the event comprises submission of a request for prior authorization for a healthcare transaction, is-submission of an insurance coverage eligibility request for a healthcare procedure, is-submission of a healthcare claim, or submission of a healthcare claim remittance.

10. A system, comprising:
one or more processors; and
at least one memory storing computer readable program code that, when executed by the one or more processors, causes the one or more processors to perform operations comprising:
receiving, by the one or more processors, an event tracking query for a patient healthcare transaction from a requestor;
receiving, by the one or more processors, a set of state transition updates for an event associated with the event tracking query from a set of different transaction processing entities that are independently controlled with respect to each other, the set of state transition updates received from the set of different transaction processing entities including one or both of (i) a set of different state identifiers and (ii) a set of different terminologies, wherein the event comprises a batch of healthcare claims;
demultiplexing, by the one or more processors, the batch of healthcare claims associated with the set of state transition updates;
mapping, by the one or more processors, the set of state transition updates to a representational workflow model, which defines a set of tracking states;
generating, by the one or more processors, an event tracking result based on the mapping of the set of state transition updates to the representational workflow model and the set of different transaction processing entities;
multiplexing, by the one or more processors, the batch of healthcare claims associated with the mapped set of state transition updates; and
transmitting, by the one or more processors, the event tracking result corresponding to the multiplexed batch of healthcare claims to the requestor.

11. The system of claim 10, wherein the set of different transaction processing entities comprises an originator, one or more intermediator entities, and one or more payors.

12. The system of claim 10, wherein the set of state transition updates comprises mappings of identifiers between ones of the set of different transaction processing entities for a set of items associated with the event; and
wherein the set of items associated with the event comprise at least one of a filename, a claim identification, a payor identification, or a provider identification.

13. The system of claim 11, wherein the set of tracking states comprises a set of high-level tracking states and a set of low-level tracking states;
wherein the set of high-level tracking states comprises one or more states indicating that a submission or a remittance for a healthcare claim is at least one of the submission or the remittance being ready for pickup by a first intermediator entity of the one or more intermediator entities, picked up by the first intermediator entity, processed by the first intermediator entity, ready for pickup by a first payor of the one or more payors, picked up by the first payor, processed by the first payor, ready for pickup by the originator, picked up by the originator, or processed by the originator; and
wherein the set of low-level tracking states comprises at least one of an identity of one of the set of different transaction processing entities currently processing the event or a custom defined state associated with one or more of the set of different transaction processing entities.

14. The system of claim 10, wherein the event tracking result indicates at least one of:
   a percentage of states complete in a life-cycle of the set of tracking states for the event; or
   a current one of the set of tracking states for the event.

15. The system of claim 10, wherein the event comprises submission of a request for prior authorization for a healthcare transaction, submission of an insurance coverage eligibility request for a healthcare procedure, submission of a healthcare claim, or submission of a healthcare claim remittance.

16. One or more non-transitory computer readable storage media storing computer readable program code that, when executed by one or more processors, causes the one or more processors to perform operations comprising:
   receiving an event tracking query for a patient healthcare transaction from a requestor;
   receiving a set of state transition updates for an event associated with the event tracking query from a set of different transaction processing entities that are independently controlled with respect to each other, the set of state transition updates received from the set of different transaction processing entities including one or both of (i) a set of different state identifiers and (ii) a set of different terminologies, wherein the event comprises a batch of healthcare claims;
   demultiplexing the batch of healthcare claims associated with the set of state transition updates;
   mapping the set of state transition updates to a representational workflow model, which defines a set of tracking states;
   generating an event tracking result based on the mapping of the set of state transition updates to the representational workflow model and the set of different transaction processing entities;
   multiplexing the batch of healthcare claims associated with the mapped set of state transition updates; and
   transmitting the event tracking result corresponding to the multiplexed batch of healthcare claims to the requestor.

* * * * *